United States Patent [19]

Tarcy

[11] Patent Number: 4,479,379
[45] Date of Patent: Oct. 30, 1984

[54] METHOD AND APPARATUS FOR CONTINUOUS ANALYSIS OF A GAS AND PARTICULATE STREAM

[75] Inventor: Gary P. Tarcy, Plum Boro, Pa.

[73] Assignee: Aluminum Company of America, Pittsburgh, Pa.

[21] Appl. No.: 497,902

[22] Filed: May 25, 1983

[51] Int. Cl.³ .................. G01N 31/00; G01N 1/22; B01D 53/00

[52] U.S. Cl. .................. 73/23; 73/863.21; 73/863.58; 55/270; 422/68; 422/69; 436/177; 436/178; 204/409

[58] Field of Search .......... 73/863.12, 863.21, 863.58, 73/23, 28; 55/270; 422/68, 69; 436/177, 178; 204/400, 409

[56] References Cited

U.S. PATENT DOCUMENTS

| | | | |
|---|---|---|---|
| 3,112,352 | 11/1963 | Krantz | 261/36 |
| 3,131,237 | 4/1964 | Collins, Jr. | 261/153 |
| 3,544,086 | 12/1970 | Willett | 261/62 |
| 3,771,289 | 11/1973 | Skoli et al. | 55/222 |
| 3,960,523 | 6/1976 | Ryan | 55/84 |
| 3,977,254 | 8/1976 | Brouwer | 73/863.21 |
| 4,096,236 | 6/1978 | Brooks et al. | 423/210 |
| 4,117,714 | 10/1978 | Goodson et al. | 73/863.21 |
| 4,134,744 | 1/1979 | Peterson et al. | 55/118 |
| 4,154,088 | 5/1979 | Werner | 73/863.12 |
| 4,263,104 | 4/1981 | Diggens et al. | 204/1 |
| 4,279,727 | 7/1981 | Scheubeck et al. | 204/409 |
| 4,354,854 | 10/1982 | Fritze et al. | 73/863.21 |

FOREIGN PATENT DOCUMENTS 737671 7/1966 Canada ............. 73/863.21

OTHER PUBLICATIONS

"Simple Liquid Scrubber for Large-Volume Air Sampling", by Lee M. Buchanan et al., *Applied Microbiology*, vol. 23, No. 6, Jun. 1972, pp. 1140-1144.

"Advances in Large-Volume Air Sampling", by Charles M. Dahlgren et al., Chemical Systems Laboratory, Aberdeen Proving Ground, Maryland, pp. 58-61.

*Primary Examiner*—Gerald Goldberg
*Assistant Examiner*—John E. Chapman, Jr.
*Attorney, Agent, or Firm*—Glenn E. Klepac

[57] ABSTRACT

The present invention discloses a method and apparatus for continuous analysis of a gas and particulate stream. More particularly, the present invention provides a method and apparatus for continuously analyzing a gas and particulate exhaust stream comprising metal fluorides to determine the fluoride concentration of such stream. A sampling nozzle communicating with a sampling line is placed in a gas and particulate stream. A gas-dissolving solvent is injected into a portion of the stream in the inlet portion of the sampling nozzle forming an aerosol. This portion of the stream and aerosol form a mixture comprising aerosol, gas and particulate which flows through the outlet portion of the sampling nozzle and through the sampling line. The aerosol in the mixture impinges against the inner surface of the sampling line wetting such inner surface with solvent; such mixture is scrubbed in the sampling line to enhance dissolution of gas in the solvent. The solvent and particulate in such mixture are separated from undissolved waste gases in the mixture, and such separated solvent and particulate are transported to a continuous analysis means to determine the concentration of dissolved gas and particulate.

17 Claims, 1 Drawing Figure

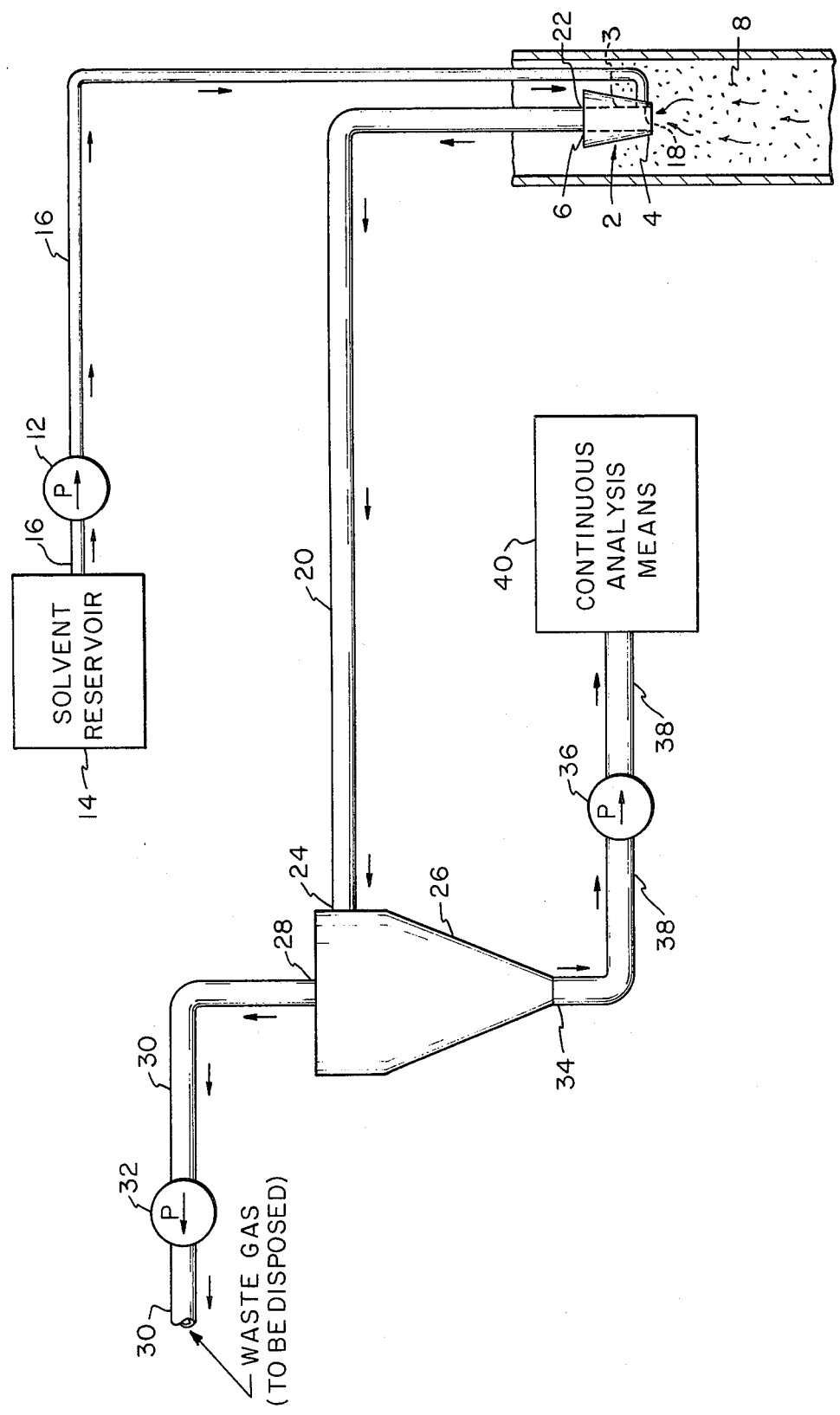

METHOD AND APPARATUS FOR CONTINUOUS ANALYSIS OF A GAS AND PARTICULATE STREAM

BACKGROUND OF THE INVENTION

The present invention relates to a method and apparatus for continuous analysis of a gas and particulate stream. More particularly, the present invention provides, for example, for continuous analysis of an exhaust stream from Hall cells in the production of aluminum comprised of gaseous and particulate metal fluorides to determine fluoride concentration in such stream.

Conventional methods of sampling gas and particulate streams generally have required a manual or semi-automatic technique for collection of the particulate species of interest. An example of such a technique has involved collection of the particulate on a filter. The particulate so collected must be analyzed at a future time by any suitable analytical method. A disadvantage of such future analysis is that such analysis provides only time-averaged historical data. If process control or process performance information is required, a method and apparatus for continuously providing a reasonably accurate sample to a means for continuous analysis is needed for efficient process control.

A significant problem with most present systems for sampling particulate containing gas streams for continuous analysis is that the sample line becomes plugged with particulate. Such plugging of the sampling line may tend to bias any analysis by failure to collect all particulate species of interest.

U.S. Pat. No. 3,960,523 to Ryan discloses an apparatus and method for the continuous sampling of effluent-bearing gas for detecting contaminants therein. In operating Ryan's apparatus, the effluent-bearing gas enters a main chamber wherein it is contacted with a vaporized scrubbing liquid to remove the effluent. The gas is then discharged from the main chamber and the vaporized liquid is condensed and introduced to a reservoir. Preferably, a continuous flow of liquid from the reservoir is maintained to an analyzer for continuous analysis for gaseous borne effluent or contaminants. Ryan indicates that the method and apparatus disclosed in the patent may be used to remove fluorides, chlorides, cyanides, ammonia and sulfides from stack gas effluent.

U.S. Pat. No. 4,134,744 to Peterson et al discloses a fine particulate captive device. The apparatus disclosed therein captures particulate matter from a gas by the flow of a dielectric fluid across a rotating disc having charged segments for the attraction of the particulate matter. The particulate matter is captured in the dielectric fluid and then centrifuged into a means for collecting the fluid.

A principal objective of the Peterson et al patent is to provide an apparatus for capturing submicron size particulate matter from a gas, such as air, for analysis. The Peterson et al patent further suggests that such apparatus be operated with a filter for capturing larger particles, thereby indicating such apparatus may not be suitable for continuous analysis of such larger particles. Also, the capture of fine particulate in the dielectric fluid in Peterson et al relies upon electrostatic potentials directed to the rotating disc and not primarily upon impingement of such particles in the dielectric fluid.

A liquid scrubber for air sampling is described in the article "Simple Liquid Scrubber for Large-Volume Air Sampling", by Buchanan et al, appearing in *Applied Microbiology*, pages 1140–1144, Volume 23, No. 6, June 1972. The principle of operation of this scrubber is founded upon producing a fine mist in a rapidly moving airstream and collecting the airborne particles by such particles impinging in a film of liquid formed by the mist droplets impacting on the walls of the scrubber. In this scrubber, the collecting fluid is pumped via a needle into the throat of an inlet arm, whereby it is transformed into a fine mist by the airstream. The mist droplets are cast from the airstream onto the scrubber walls, thereby forming a continuous, helically moving liquid film. The airborne particles primarily are taken out of the airstream through impingement in this liquid film. Such liquid film is moved by the airstream to an outlet where fluid collection in a flask occurs assisted by applying a slight vacuum.

The Buchanan et al article on the liquid scrubber discussed in the previous paragraph indicates such scrubber is mainly applicable to the recovery of microorganisms from large volumes of air, or for use in work relating to airborne disease transmission. This article does not disclose or suggest whether such liquid scrubber could be used for sampling other forms of particulate or various particulate containing stack gases, such as Hall cell fume, for example. Regarding such other forms of particulate and stack gases, this article does not disclose whether such scrubber has any means for transporting an unbiased, representative sample of particulate species of interest from a stream source to such scrubber, if such scrubber could be so used for such particulate or if such scrubber could not be physically located in such stream.

In the paper "Advances in Large-Volume Air Sampling", by Dahlgren et al, apparently originating at the Chemical Systems Laboratory, Aberdeen Proving Ground, Md., various sampling devices are described for use in the collection of viable microorganisms from air. This paper discloses, inter alia, an air-to-air concentrator-wet collector having three stages. In the first two stages, selected particles of a specific size are concentrated into a lesser defined air volume. In the third stage, such concentrated sample volume is directed to a liquid scrubber, whereby the particles therein are removed from the airstream by impinging in a small amount of collecting fluid.

The Dahlgren et al paper of the previous paragraph describes the air-to-air concentrator-wet collector as being designed primarily for operation in ambient air for sampling viable microorganisms therefrom. This paper does not disclose whether such collector is suitable for other non-related sampling applications, such as sampling process streams comprised of various stack gases, for example. The Dahlgren et al paper does not indicate whether particulate plugging in any stage of such collector or in any sampling line bringing a particulate-containing stream to such collector would occur, if such collector were used for purposes not stated in this paper. As previously mentioned, particulate plugging in the sampling system or in any delivery line thereto may bias any analysis through the inability to collect a representative sample of the particulate.

What is needed, therefore, is a simple and efficient method and apparatus for continuous analysis of a gas and particulate stream from a variety of sources. Such method and apparatus should provide for collection of particulate species of interest to permit accurate and unbiased continuous analysis thereof.

SUMMARY OF THE INVENTION

The present invention relates to a method and apparatus for continuous analysis of a gas and particulate stream. More particularly, the present invention provides for continuous analysis of various process streams comprised of metal halides, metal sulfates, metal nitrates, metal phosphates or $C_4$–$C_{20}$ hydrocarbons, excluding waxes and tars.

The present invention provides a method for continuous analysis of a gas and particulate stream in an apparatus comprising an elongated sampling line, a sampling nozzle, injector means, separator means, transport means and continuous analysis means. The elongated sampling line has a first end and a second end spaced from the first end. The sampling nozzle, communicating with the first end of the sampling line, has an aerodynamic shape to provide isokinetic sampling of the gas and particulate stream and has an inlet portion and an outlet portion. The injector means injects a gas-dissolving solvent in the nozzle inlet portion. The separator means separates solvent and particulate from undissolved waste gases, the separator means being in communication with the second end of the sampling line. The transport means transports the separated solvent and particulate from the separator means to a continuous analysis means. The continuous analysis means analyzes the dissolved gas and particulate.

Accordingly, in such apparatus, the method of the present invention comprises the steps of:

(a) injecting gas-dissolving solvent into a portion of a gas and particulate stream in the nozzle inlet portion to form an aerosol in such portion of the stream;

(b) collecting in the sampling nozzle such portion of the stream and aerosol to form a mixture comprising aerosol, gas and particulate;

(c) flowing such mixture through the outlet portion of the sampling nozzle into the sampling line;

(d) transporting such mixture in the sampling line to the separator means;

(e) impinging the aerosol against the inner surface of the sampling line to wet such inner surface with solvent;

(f) scrubbing such mixture in the sampling line to enhance dissolution of gas in the solvent;

(g) separating the solvent and particulate in such mixture from undissolved waste gases in such mixture;

(h) transporting the separated solvent and particulate to a continuous analysis means; and (i) continuously analyzing to determine the concentration of dissolved gas and particulate.

An objective of the present invention is to provide a simple and efficient method and apparatus for continuous analysis of a gas and particulate stream.

A further objective of the present invention is to provide a method and apparatus for collection of gas and particulate species of interest permitting accurate and unbiased continuous analysis of such species.

An additional objective of the present invention is to provide a method and apparatus for continuous analysis of Hall cell fume in the production of aluminum to continuously determine the total fluoride concentration of such fume.

The above-mentioned and other objectives and advantages of the present invention will be more fully appreciated and understood by reference to the following detailed description and the drawing appended hereto.

BRIEF DESCRIPTION OF THE DRAWING

The sole FIGURE is a schematic representation illustrating the method and apparatus of the present invention.

DESCRIPTION OF THE PREFERRED EMBODIMENTS

Referring to the FIGURE, a schematic representation of a preferred method and apparatus of the present invention is illustrated. The method and apparatus of the present invention is highly useful in providing Hall cell process control information in the manufacture of aluminum by continuously analyzing fumes to determine the fluoride concentration, though the invention is not limited thereto.

This FIGURE shows a sampling nozzle 2 having an inlet portion 4 and an outlet portion 6. Nozzle 2 has an aerodynamic shape to provide for isokinetic sampling of a gas and particulate stream 8. Preferably, nozzle 2 has a frustoconical-shaped inlet portion 4 to promote isokinetic sampling of stream 8. Nozzle 2 desirably also has channel 3 for flowing therethrough a portion of stream 8 and an aerosol, discussed hereinafter.

An injector means is provided for injecting a gas-dissolving solvent into a portion of stream 8 in nozzle inlet portion 4 to form an aerosol. The injector means comprises a solvent transport pump 12, a solvent reservoir 14 and a solvent delivery line 16. The solvent transport pump 12 communicates with solvent reservoir 14 and inlet portion 4 of nozzle 2 by means of solvent delivery line 16. Solvent delivery line 16 has an opening 18 which is suitably located in the interior of nozzle inlet portion 4. Preferably, opening 18 is situated substantially close to the entering point of stream 8 into inlet portion 4. Solvent delivery line 16 should be comprised of material that is substantially inert to stream 8 and the gas-dissolving solvent being injected, such as polytetrafluoroethylene, for example.

An elongated sampling line 20 having a first end 22 and a second end 24 communicates at first end 22 with an outlet portion 6 of the sampling nozzle 2. Such communication allows that portion of stream 8 and aerosol flowing through nozzle 2 in channel 3 to flow through sampling line 20. In flowing through sampling line 20 the aerosol impinges against the inner surface of the sampling line 20 to wet such inner surface with solvent, thereby transporting the solvent and particulate through sampling line 20 and scrubbing that portion of stream 8 flowing in line 20 to enhance dissolution of gas in the solvent.

It is desirable that the inner surface of sampling line 20 have a large surface area to promote scrubbing. It is also desirable that sampling line 20 have an inner diameter of at least about 5 mm to insure an adequate surface area to aid such scrubbing. Sampling line 20 can be flexible or rigid in construction, depending upon the individual sampling need. While the outward shape of sampling line 20 can be any number of suitable configurations, such as rectangular-shaped or square-shaped, for example, it is most desirable that sampling line 20 be cylindrical-shaped in the form of a tube. It is further desirable that channel 3 substantially conform in shape to the shape of line 20.

Sampling line 20 is elongated and is not generally limited to any particular length. The length of sampling line 20 is primarily determined by the particular sampling application and the location of the apparatus used in practicing the present invention from the gas and particulate stream. For example, the length of line 20 could be upwards of 500 feet if various stack gases are being sampled for continuous analysis, since conditions at such sample source would not be conducive to placing the remainder of the apparatus of the present invention near such source location. On the other hand, sampling line 20 could be about one or two feet in length in other sampling applications. However, line 20 should desirably be of sufficient length to insure adequate scrubbing of the gas and particulate stream. Wetting of sampling line 20 substantially minimizes particulate loss by preventing particulate from adhering to the inner surface of the sampling line or preventing particulate from plugging the sampling line near the ends thereof.

It is desirable that the material comprising elongated sampling line 20 and sampling nozzle 2 be substantially inert to stream 8 and have a low coefficient of friction relative to stream 8. It is preferable that such material for line 20 and nozzle 2 be comprised of a fluoropolymer and, more preferably, such fluoropolymer is polytetrafluoroethylene. Polyvinyl chloride or stainless steel may also be used, depending upon the particular application. Examples of suitable materials for line 20 and nozzle 2 when determining the concentration of metal halides, particularly metal fluorides, are polytetrafluoroethylene and polyvinyl chloride.

A separator means 26 communicates with the second end 24 of elongated sampling line 20. Separator means 26 separates the solvent and particulate from undissolved waste gases in the portion of stream 8 flowing therethrough.

The separator means 26 desirably has a waste gas outlet 28 for discharging waste gas from the separator means 26. As shown in the figure, it is also desirable that waste gas outlet 28 be connected to a gas disposal conduit 30 which communicates with a gas transport pump 32 to aid in removing undissolved waste gases from separator means 26, although conduit 30 and pump 32 are not essential to the invention. A solvent and particulate outlet 34 is provided in separator means 26 for exit of the separated solvent and particulate from separator means 26.

It is desirable that separator means 26 comprises a cyclone separator, as is shown in the figure. The operation of such cyclone separator is known to those skilled in the art. Separator means 26 should preferably be comprised of a material that is substantially inert to the portion of stream 8 flowing therethrough. An example of a suitable material for the separator means 26 is glass, particularly if the concentration of metal halides in a gas and particulate stream is to be determined by continuous analysis.

A transport means is provided for transporting the separated solvent and particulate from separator means 26 to a means for continuous analysis, discussed hereinafter. The transport means preferably comprises a liquid transport pump 36 and a transport line 38. Transport line 38 connects pump 36 with outlet 34 of separator means 26, the separator means desirably being a cyclone separator as previously mentioned. Transport line 38 also places pump 36 in communication with continuous analysis means 40.

Continuous analysis means 40 in communication with the transport means, as previously discussed, determines the concentration of dissolved gas and particulate of interest. The particulate matter is extracted with a suitable extractant in order to bring into solution the component of interest so that such component can be analyzed. Continuous analysis means 40 can also be utilized to determine only the concentration of dissolved gas or only the concentration of particulate of interest in stream 8.

The apparatus of the present invention, previously discussed, is useful for continuous analysis of stream 8 where stream 8 comprises a substance selected from the group consisting of metal halides, metal fluorides, metal sulfates, metal nitrates, metal phosphates and $C_4$–$C_{20}$ hydrocarbons, excluding waxes and tars. Continuous analysis means 40 determines the concentration of such selected substance. The apparatus of the present invention is particularly advantageous for continuous analysis of sodium and aluminum salts of metal halides found in various stack gases, such as sodium fluoride and aluminum fluoride.

In operation, the method of the present invention for continuous analysis of a gas and particulate stream in the apparatus of the present invention comprises the following steps. A gas dissolving solvent is injected into a portion of a gas and particulate stream 8 in nozzle inlet portion 4 to form an aerosol in such portion of stream 8. Preferably, the solvent comprises water, more preferably, deionized water, and a surfactant. The surfactant aids in retaining the particulate in the impinged aerosol, comprising substantially water in most preferred embodiments of the invention, and lowers the surface tension of the water to facilitate the flow over the inner surface of the sampling line. Such solvent is useful when analyzing for metal halides. When analyzing for fluoride concentration, it is desirable that the solvent further comprise KBr dissolved in the solvent including water and surfactant. The dissolved KBr provides an internal reference solution in a method similar to that discussed in my copending application entitled "Measurement of Gaseous Fluoride Concentration Using an Internal Reference Solution" having U.S. Ser. No. 418,286, filed on Sept. 15, 1982, now U.S. Pat. No. 4,428,800, hereby incorporated by reference. In analyzing for the fluoride concentration of Hall cell fume in the method of the present invention, the solvent preferably is injected at a rate of about 5 ml/min, although other flow rates may be employed depending upon the choice of solvent, analysis system parameters and the purpose for which the method of the invention is being applied.

Such portion of stream 8 flowing in nozzle inlet portion 4 and the aerosol is collected in sampling nozzle 2 to form a mixture comprising aerosol, gas and particulate.

Such mixture is then flowed through outlet portion 6 of sampling nozzle 2 into elongated sampling line 20. When analyzing to determine the fluoride concentration in exhaust gases from Hall cells in the production of aluminum, it is desired that the flow rate, or sampling rate, flowing through nozzle 2 and sampling line 20 be in the range of about 16 l/min to about 25 l/min.

Such mixture is transported through sampling line 20 to separator means 26. The aerosol is impinged against the inner surface of line 20 to wet such inner surface with solvent aiding in transporting such mixture in line 20, as previously indicated, and such mixture is scrubbed in line 20 to enhance dissolution of gas in the solvent.

The solvent and particulate in such mixture are separated from undissolved waste gases in separator means 26. The separated solvent and particulate are transported via the transport means, comprising in a preferred embodiment transport line 38 and pump 36, to continuous analysis means 40. The dissolved gas and particulate are continuously analyzed in continuous analysis means 40 to determine their concentration.

Depending upon the information desired, the continuous analysis in analyzer 40 in the method of the present invention can be only to determine the concentration of dissolved gas or only the concentration of particulate species of interest.

Like the apparatus of the present invention, the method of the present invention is applicable for continuously analyzing a gas and particulate stream where such stream comprises a substance selected from the group consisting of metal halides, metal fluorides, metal sulfates, metal nitrates, metal phosphates and $C_4$–$C_{20}$ hydrocarbons, excluding waxes and tars. Analysis means 40 continuously analyzes to determine the concentration of such substance of interest.

The following example is offered as being illustrative of the method and apparatus of the present invention, although the present invention should not be construed as being limited thereto.

The method of the present invention was applied in an apparatus of the present invention to the sampling of fumes from Hall cells to determine the fluoride concentration therein. The solvent used was comprised of deionized water, 0.5 ml per liter TRITON X-100 (a nonionic surfactant), and 100 mg per liter dissolved KBr. The solvent injection rate was about 5 ml/min and the sampling rate or flow rate through the sampling nozzle and the sampling line was in the range of about 16 l/min to about 25 l/min. In the test runs, a filter and a bubble trap were used for the purpose of determining the scrubbing efficiency, though such filter and bubble trap are not strictly a part of the present invention. The filter primarily collected any particulate fluoride in the waste gas and the bubble trap primarily collected any gaseous fluoride in the waste gas. The scrubbing efficiency expressed as a percentage was determined using the following formula:

$$\% \text{ scrubbing efficiency} = \left[ \frac{\text{fluoride sample collected*}}{\text{filter + bubble trap + fluoride sample collected*}} \right] \times 100$$

(*fluoride sample collected = sample collected by method and apparatus of present invention)

In the test runs performed, substantially no fluoride was ever found in the bubble trap, indicating the method and apparatus of the present invention was substantially 100% efficient for collecting gaseous fluoride for continuous analysis.

The following table illustrates ten test runs utilizing the present invention showing % scrubbing efficiency and total fluoride collected (gas and particulate) for continuous analysis in each run. The sampling line for these ten tests was comprised of either polytetrafluoroethylene or polyvinyl chloride. Polytetrafluoroethylene is most preferred in sampling fluoride-containing fumes from Hall cells.

TABLE

| Test No. | % Scrubbing Efficiency | Total mg Fluoride Collected (gas and particulate) |
|---|---|---|
| 1 | 94 | 1068 |
| 2 | 93 | 614 |
| 3 | 93 | 158 |
| 4 | 96 | 82.6 |
| 5 | 93 | 48.8 |
| 6 | 93 | 340.6 |
| 7 | 95 | 211.6 |
| 8 | 98 | 223.7 |
| 9 | 98 | 307.1 |
| 10 | 99 | 600.9 |

While the present invention has been described in terms of preferred embodiments, it will be apparent to those skilled in the art that certain modifications and adaptations within the scope of the present invention can be made to the method and apparatus based upon the teachings presented herein and would be consistent with the invention as defined in the claims hereto appended.

What is claimed is:

1. A method for continuous analysis of a gas and particulate stream in an apparatus comprising:
    (i) an elongated sampling line having a first end and a second end spaced from said first end;
    (ii) a sampling nozzle communicating with the first end of said sampling line having an aerodynamic shape to provide isokinetic sampling and having an inlet portion and an outlet portion;
    (iii) injector means for injecting a gas-dissolving solvent in said nozzle inlet portion;
    (iv) separator means for separating solvent and particulate from undissolved waste gases, said separator means being in communication with the second end of said sampling line;
    (v) transport means for transporting the separated solvent and particulate from the separator means to a continuous analysis means; and
    (vi) continuous analysis means for analyzing the dissolved gas and particulate;
said method comprising the steps of:
    (a) injecting gas-dissolving solvent into a portion of a gas and particulate stream in said nozzle inlet portion to form an aerosol in said portion of said stream;
    (b) collecting in said sampling nozzle said portion of said stream and aerosol to form a mixture comprising aerosol, gas and particulate;
    (c) flowing said mixture through the outlet portion of said sampling nozzle into said sampling line;
    (d) transporting said mixture in said sampling line to said separator means;
    (e) impinging the aerosol against the inner surface of said sampling line to wet said inner surface with solvent;
    (f) scrubbing said mixture in said sampling line to enhance dissolution of gas in the solvent;
    (g) separating the solvent and particulate in said mixture from undissolved waste gases in said mixture;
    (h) transporting said separated solvent and particulate to a continuous analysis means; and
    (i) continuously analyzing to determine the concentration of dissolved gas and particulate.

2. The method of claim 1 wherein said stream comprises a substance selected from the group consisting of metal halides, metal fluorides, metal sulfates, metal nitrates, metal phosphates and $C_4$–$C_{20}$ hydrocarbons, excluding waxes and tars; and step (i) comprises continuously analyzing to determine the concentration of said substance.

3. The method of claim 1 wherein said solvent comprises water and surfactant dissolved in said water.

4. The method of claim 3 wherein said solvent further comprises dissolved KBr.

5. The method of claim 1 wherein step (i) comprises continuously analyzing to determine only the concentration of dissolved gas.

6. The method of claim 1 wherein step (i) comprises continuously analyzing to determine only the concentration of particulate.

7. An apparatus for continuous analysis of a gas and particulate stream, said apparatus comprising:
 (a) a sampling nozzle having an inlet portion and an outlet portion, said nozzle having an aerodynamic shape to provide isokinetic sampling of said stream;
 (b) injector means for injecting a gas-dissolving solvent into a portion of said gas and particulate stream in said nozzle inlet portion to form an aerosol;
 (c) an elongated sampling line having a first end and a second end spaced from said first end, said first end of said sampling line communicating with the outlet portion of said nozzle for flowing therethrough said portion of said gas and particulate stream and aerosol thereby impinging the aerosol against the inner surface of said sampling line to wet said inner surface with solvent and thereby scrubbing said portion of said stream flowing therethrough to enhance dissolution of gas in the solvent;
 (d) separator means for separating solvent and particulate from undissolved waste gases in said portion of said stream, said separator means being in communication with the second end of said sampling line;
 (e) transport means for transporting the separated solvent and particulate from the separator means to a continuous analysis means; and
 (f) continuous analysis means for determining the concentration of dissolved gas and particulate, said continuous analysis means being in communication with said transport means.

8. The apparatus of claim 7 wherein said stream comprises a substance selected from the group consisting of metal halides, metal fluorides, metal sulfates, metal nitrates, metal phosphates and $C_4$–$C_{20}$ hydrocarbons, excluding waxes and tars; and said continuous analysis means determines the concentration of said substance.

9. The apparatus of claim 7 wherein the material comprising said sampling nozzle and said sampling line is substantially inert to said stream and has a low coefficient of friction relative to said stream.

10. The apparatus of claim 7 wherein the material comprising said sampling nozzle and said sampling line is a fluoropolymer.

11. The apparatus of claim 10 wherein said fluoropolymer is polytetrafluoroethylene.

12. The apparatus of claim 7 wherein said sampling line has an inner diameter of at least about 5 mm.

13. The apparatus of claim 7 wherein said separator means comprises a cyclone separator.

14. The apparatus of claim 13 wherein said transport means comprises a liquid transport pump connected with said cyclone separator.

15. The apparatus of claim 7 wherein said injector means comprises a solvent transport pump.

16. The apparatus of claim 7 wherein said continuous analysis means determines only the concentration of dissolved gas.

17. The apparatus of claim 7 wherein said continuous analysis means determines only the concentration of particulate.

* * * * *